(12) United States Patent
Cosmescu

(10) Patent No.: US 12,096,979 B2
(45) Date of Patent: Sep. 24, 2024

(54) ULTRAPOLAR TELESCOPIC ELECTROSURGERY PENCIL AND ULTRAPOLAR ELECTROSURGERY BLADE

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

(*) Notice: Subject to any disclaimer, the term of this patent is extended or adjusted under 35 U.S.C. 154(b) by 0 days.

(21) Appl. No.: 18/148,033

(22) Filed: Dec. 29, 2022

(65) Prior Publication Data

US 2023/0135303 A1 May 4, 2023

Related U.S. Application Data

(63) Continuation of application No. 15/725,640, filed on Oct. 5, 2017, now Pat. No. 11,564,740.
(Continued)

(51) Int. Cl.
*A61B 18/14* (2006.01)
*A61B 18/16* (2006.01)
(Continued)

(52) U.S. Cl.
CPC .......... *A61B 18/16* (2013.01); *A61B 18/1402* (2013.01); *A61B 2017/00991* (2013.01); *A61B 2018/00077* (2013.01); *A61B 2018/00083* (2013.01); *A61B 2018/00178* (2013.01); *A61B 2018/00607* (2013.01);
(Continued)

(58) Field of Classification Search
CPC ... A61B 18/1402; A61B 18/14; A61B 18/148; A61B 2018/00601; A61B 2018/1497; A61B 2018/00607; A61B 2018/126; A61B 2018/1412; A61B 2018/1475; A61B 2018/162; A61B 2018/00077; A61B 2018/00083; A61B 2018/00148; A61B 2018/0016; A61B 2017/00991; A61B 2218/007; A61B 2218/008
USPC ........ 606/37, 39, 41, 45, 48, 50; 607/98, 99, 607/101, 113, 115, 116
See application file for complete search history.

(56) References Cited

U.S. PATENT DOCUMENTS 4,232,676 A 11/1980 Herczog
4,802,476 A * 2/1989 Noerenberg ....... A61B 18/1402
606/50
(Continued)

OTHER PUBLICATIONS

International Search Report and Written Opinion in related PCT application No. PCT/US2017/055415 mailed Dec. 1, 2017, 10 pages.

*Primary Examiner* — Thomas A Giuliani
(74) *Attorney, Agent, or Firm* — Zeman-Mullen & Ford, LLP

(57) ABSTRACT

An ultrapolar telescopic electrosurgery pencil that can be used in both monopolar and bipolar modes for cutting and coagulation. The ultrapolar telescopic electrosurgery pencil can operate at very low power levels (such as 15-20 Watts or less) to both cut and coagulate tissue thereby reducing patient risk and damage to tissue. An ultrapolar electrosurgery blade having a top, a bottom, opposing planar sides, a cutting edge, and a non-cutting end, an active electrode positioned on one of the opposing planar sides such that at least a portion of the opposing planar side is exposed near the cutting edge, and a return electrode positioned on the other opposing planar side such that at least a portion of the other opposing side is exposed near the cutting edge.

20 Claims, 5 Drawing Sheets

Related U.S. Application Data

(60) Provisional application No. 62/404,292, filed on Oct. 5, 2016.

(51) Int. Cl.
*A61B 17/00* (2006.01)
*A61B 18/00* (2006.01)
*A61B 18/12* (2006.01)

(52) U.S. Cl.
CPC . *A61B 2018/00952* (2013.01); *A61B 18/1206* (2013.01); *A61B 2018/1253* (2013.01); *A61B 2018/126* (2013.01); *A61B 2018/1412* (2013.01); *A61B 2018/1475* (2013.01); *A61B 2018/162* (2013.01); *A61B 2218/007* (2013.01); *A61B 2218/008* (2013.01)

(56) References Cited

U.S. PATENT DOCUMENTS

| | | |
|---|---|---|
| 4,850,353 A | 7/1989 | Stasz et al. |
| 7,070,604 B1 | 7/2006 | Garito et al. |
| 8,444,641 B2 | 5/2013 | Huseman |
| 10,512,500 B2 | 12/2019 | Cosmescu |
| 10,702,334 B2 | 7/2020 | Cosmescu |
| 11,395,693 B2 * | 7/2022 | Cosmescu ............ A61B 18/082 |
| 11,564,740 B2 * | 1/2023 | Cosmescu .......... A61B 18/1402 |
| 2003/0130658 A1 | 7/2003 | Goble et al. |
| 2005/0113825 A1 * | 5/2005 | Cosmescu .......... A61B 18/1402 |
| | | 606/49 |
| 2005/0283151 A1 | 12/2005 | Ebbutt et al. |
| 2009/0018539 A1 | 1/2009 | Cosmescu |
| 2018/0250057 A1 | 9/2018 | Cosmescu |
| 2018/0250071 A1 | 9/2018 | Cosmescu |
| 2020/0121383 A1 | 4/2020 | Cosmescu |
| 2022/0338918 A1 * | 10/2022 | Cosmescu .......... A61B 18/1402 |

\* cited by examiner

ULTRAPOLAR TELESCOPIC ELECTROSURGERY PENCIL AND ULTRAPOLAR ELECTROSURGERY BLADE

CROSS REFERENCE TO RELATED APPLICATIONS

This application is a continuation patent application of utility patent application having Ser. No. 15/725,640, issued as U.S. Pat. No. 11,564,740 on Jan. 31, 2023, which claims priority to provisional patent application having Ser. No. 62/404,292 entitled "Ultrapolar Telescopic Electrosurgery Pencil," filed Oct. 5, 2016, which are herein incorporated by reference in their entireties. This application also relates to patent application having Ser. No. 15/697,335 entitled "Ultrapolar Electrosurgery Blade and Pencil For Use In ESU Monopolar And Bipolar Modes" which is also herein incorporated by reference in its entirety.

FIELD OF INVENTION

The present invention is generally directed to an ultrapolar telescopic electrosurgery pencil for use in both monopolar mode and bipolar mode for cutting and coagulation. The ultrapolar telescopic electrosurgery pencil includes a handpiece member having first and second ends, a hollow telescopic member having first and second ends where at least a portion of the hollow telescopic member is concentrically positioned within the first end of the handpiece member, and an electrosurgery blade positioned within the first end of the hollow telescopic member where the electrosurgery blade includes a nonconductive member with opposing planar sides and a cutting edge, an active electrode positioned on one of the opposing planar sides such that at least a portion of the opposing planar side is exposed near the cutting edge, and a return electrode positioned on the other opposing planar side such that at least a portion of the other opposing planar side is exposed near the cutting edge. The hollow telescopic member and the handpiece member may also form an evacuation channel for evacuating smoke and/or debris away from the surgical site.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monopolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy and thereby reduces or eliminates the likelihood of tissue damage and sparking associated with monopolar electrosurgery, it has limited ability to cut and coagulate large bleeding areas.

Accordingly, there is a need for an electrosurgery blade and an electrosurgery pencil that can be used in both monopolar and bipolar modes for cutting and coagulation thereby allowing flexibility for cutting and coagulation of large areas of tissue without the tissue damage when used in monopolar mode and which eliminates passing of energy through the patient when used in bipolar mode. An ultrapolar telescopic electrosurgery pencil with an ultrapolar electrosurgery blade having a sharp cutting end and an active electrode positioned on one opposing planar side of a non-conductive member and a return electrode positioned on the other opposing planar side of the non-conductive member would meet this need. The ultrapolar telescopic electrosurgery pencil described with reference to the present invention can be used in both monopolar and bipolar modes thereby providing flexibility to a surgeon or operator. The ultrapolar telescopic electrosurgery pencil described with reference to the present invention also enables a user or surgeon to more easily and efficiently access the surgical site with enhanced viewing capability by extending the telescopic member of the pencil as well as the electrosurgery blade positioned within the telescopic member of the pencil. Some embodiments of the ultrapolar telescopic electrosurgery pencil described with reference to the present invention also enable a user or surgeon to evacuate smoke and/or debris form the surgical site while being able to perform precise cutting at the surgical site as well as cutting and coagulation of tissue areas located at the surgical site.

SUMMARY OF THE INVENTION

The present invention is directed to an ultrapolar telescopic electrosurgery pencil which includes a handpiece member having first and second ends, a hollow telescopic member having first and second ends with the second end of the hollow telescopic member concentrically positioned within the first end of the handpiece member, and an electrosurgery blade positioned at least partially within the first end of the hollow telescopic member where the electrosurgery blade includes a non-conductive member with opposing planar sides and a cutting edge, an active electrode positioned on one of the opposing planar sides so that at least a portion of the opposing planar side is exposed near the cutting edge, and a return electrode positioned on the other opposing planar side so that at least a portion of the other opposing sides is exposed near the cutting edge. The ultrapolar telescopic electrosurgery pencil can be used in both a monopolar mode and a bipolar mode when used to perform electrosurgery. In addition, the ultrapolar telescopic electrosurgery pencil of the present invention is capable of cutting and coagulating tissue at a low power level, namely a power level that is less than 20 watts.

The ultrapolar telescopic electrosurgery pencil may include a retaining member located within the hollow telescopic member for retaining at least a portion of the electrosurgery blade within the telescopic member. The handpiece member and the hollow telescopic member may form an evacuation channel for evacuating smoke and/or debris away from the surgical site where the ultrapolar telescopic electrosurgery pencil is being employed.

A nozzle member may be connected to the first end of the hollow telescopic member so that at least a portion of the electrosurgery blade is positioned in the nozzle member as well as within the first end of the hollow telescopic member. The ultrapolar telescopic electrosurgery pencil may also include a swivel member connected to the second end of the handpiece member to inhibit twisting and kinking of a vacuum tube connected to the electrosurgery pencil for evacuating smoke and/or debris from the surgical site. In embodiments of the ultrapolar telescopic electrosurgery pencil of the present invention that accommodate evacuation of smoke and/or debris from the surgical site, the nozzle, hollow telescopic member, handpiece member, and swivel member may all form part of an evacuation channel for diverting smoke and/or debris away from the surgical site.

In one exemplary embodiment, the ultrapolar telescopic electrosurgery pencil of the present invention includes a handpiece member having first and second ends, a hollow telescopic member having first and second ends with the second end of the hollow telescopic member concentrically positioned within the first end of the handpiece member, and an electrosurgery blade positioned at least partially within the first end of the hollow telescopic member where the electrosurgery blade includes a non-conductive member with opposing planar sides and a cutting edge, an active electrode positioned on one of the opposing planar sides so that at least a portion of the opposing planar side is exposed near the cutting edge, and a return electrode positioned on the other opposing planar side so that at least a portion of the other opposing sides is exposed near the cutting edge, a first insulated wire connected to the active electrode of the electrosurgery blade and a first retaining element for retaining at least a portion of the first insulated wire near a top interior of the handpiece member, and a second insulated wire connected to the return electrode of the electrosurgery blade and a second retaining element for retaining at least a portion of the second insulated wire near a bottom interior of the handpiece member. This exemplary embodiment may also include the nozzle and swivel members previously described above and the nozzle member, hollow telescopic member, handpiece member, and swivel member may form an evacuation channel for evacuating smoke and/or debris away from the surgical site.

In another exemplary embodiment, the ultrapolar telescopic electrosurgery pencil of the present invention includes a handpiece member having first and second ends, a hollow telescopic member having first and second ends with the second end of the hollow telescopic member concentrically positioned within the first end of the handpiece member, and an electrosurgery blade positioned at least partially within the first end of the hollow telescopic member where the electrosurgery blade includes a non-conductive member with opposing planar sides and a cutting edge, an active electrode positioned on one of the opposing planar sides so that at least a portion of the opposing planar side is exposed near the cutting edge, and a return electrode positioned on the other opposing planar side so that at least a portion of the other opposing sides is exposed near the cutting edge, a conductive elongated contact member attached to a top interior surface of the handpiece member and a conductive contact member connected to the active electrode of the electrosurgery blade such that the conductive contact member can be slidably engaged with respect to the conductive elongated contact member, and a hollow conductive tube member contained within the hollow telescopic member that is connected to the return electrode of the electrosurgery blade and a solid conductive rod member connected to the handpiece member such that the solid conductive rod member can slide within and along a length of the hollow conductive tube member.

In this second exemplary embodiment, at least a portion of the conductive contact member may be positioned within and interior of the hollow telescopic member and at least a portion of the conductive contact member may be positioned on an exterior surface of the conductive contact member. In addition, instead of a hollow conductive tube member contained within the hollow telescopic member and connected to the return electrode of the electrosurgery blade, it could be a solid conductive rod contained within the hollow telescopic member and connected to the return electrode of the electrosurgery blade. In this case, instead of a solid conductive rod connected to the handpiece member, a hollow conductive tube member would be connected to the handpiece member so that the solid conductive rod contained within the hollow telescopic member could slide within the hollow conductive tube member contained within the handpiece member. Like the first exemplary embodiment described above, this second exemplary embodiment may also include the nozzle and swivel members previously described and the nozzle member, hollow telescopic member, handpiece member, and swivel member may form an evacuation channel for evacuating smoke and/or debris away from the surgical site.

The ultrapolar telescopic electrosurgery pencil of the present invention can be used in both monopolar and bipolar modes when used to perform electrosurgery. The insulated wire or conductive contact member in the electrosurgery pencil that is in communication with the active electrode of the electrosurgery blade is connected to a circuit board contained within the electrosurgery pencil for activating the electrosurgery pencil and the circuit board is in turn connected to an electrosurgery unit generator through an electrical connection means such as a wire. In addition, the insulated wire or conductive rod or hollow member that is in communication with the return electrode of the electrosurgery blade is also connected to the electrosurgery unit generator through an electrical connection means such as a wire so that both the active and return contacts of the ultrapolar electrosurgery blade in the ultrapolar telescopic electrosurgery pencil are connected to the electrosurgery unit generator. When the ultrapolar telescopic electrosurgery pencil of the present invention is used in monopolar mode, the monopolar power output mode is selected on the electrosurgical unit generator. When the ultrapolar telescopic electrosurgery pencil of the present invention is used in bipolar mode, the bipolar power output mode is selected on the electrosurgical unit generator.

BRIEF DESCRIPTION OF THE DRAWINGS

The subject invention will hereafter be described in conjunction with the appended drawing figures, wherein like numerals denote like elements.

Figure 1:
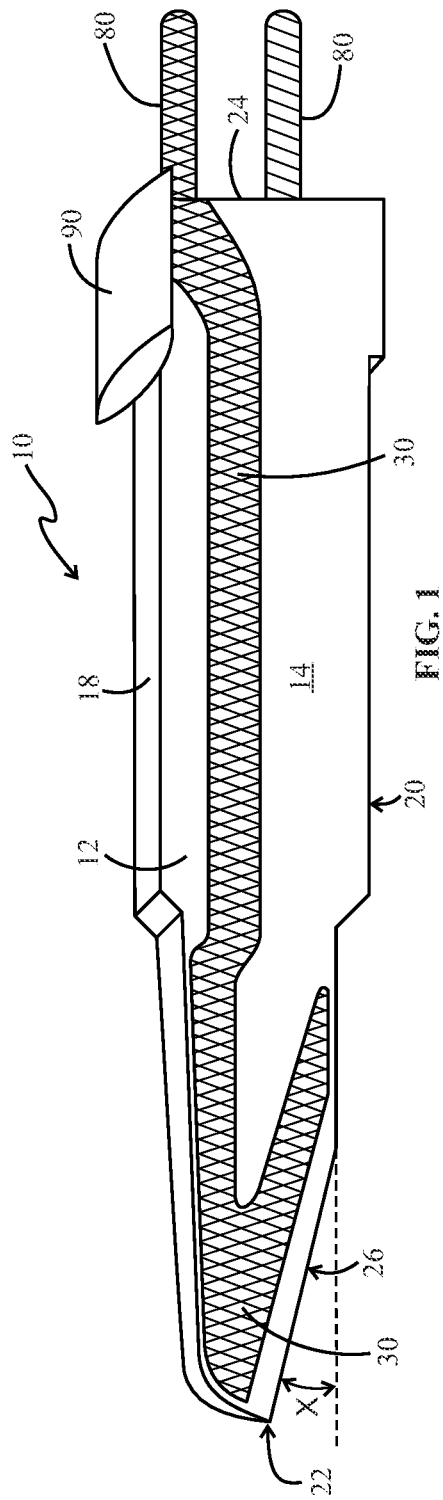
FIG. 1 is a side perspective view of an exemplary embodiment of an ultrapolar electrosurgery blade used in the ultrapolar telescopic electrosurgery pencil of the present invention.
Figure 2:
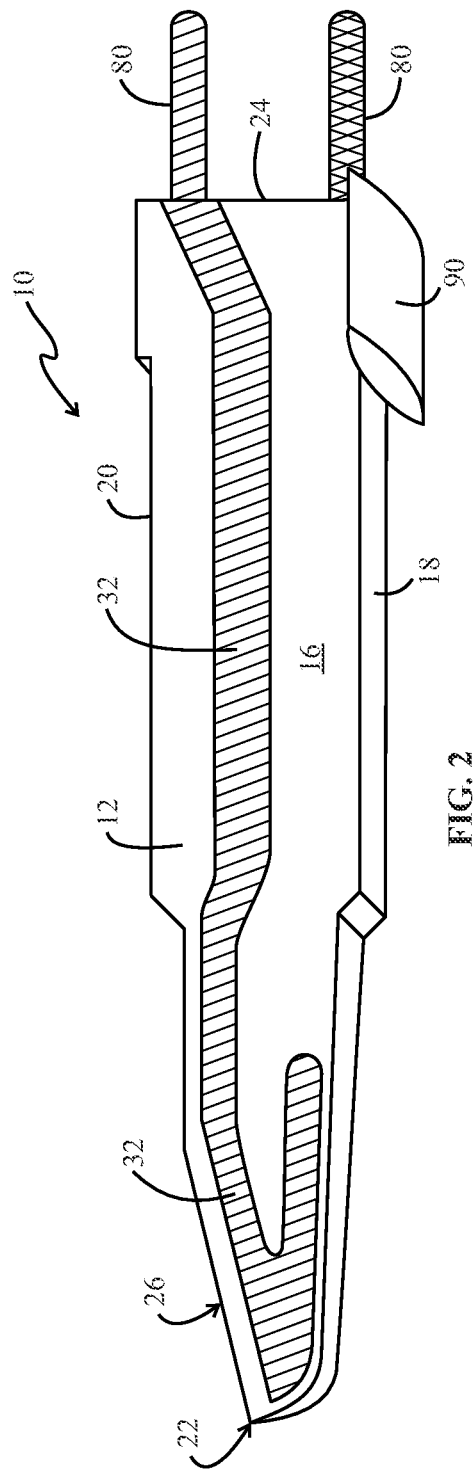
FIG. 2 is an opposite side view of the exemplary embodiment of the ultrapolar electrosurgery blade shown in FIG. 1.
Figure 4:
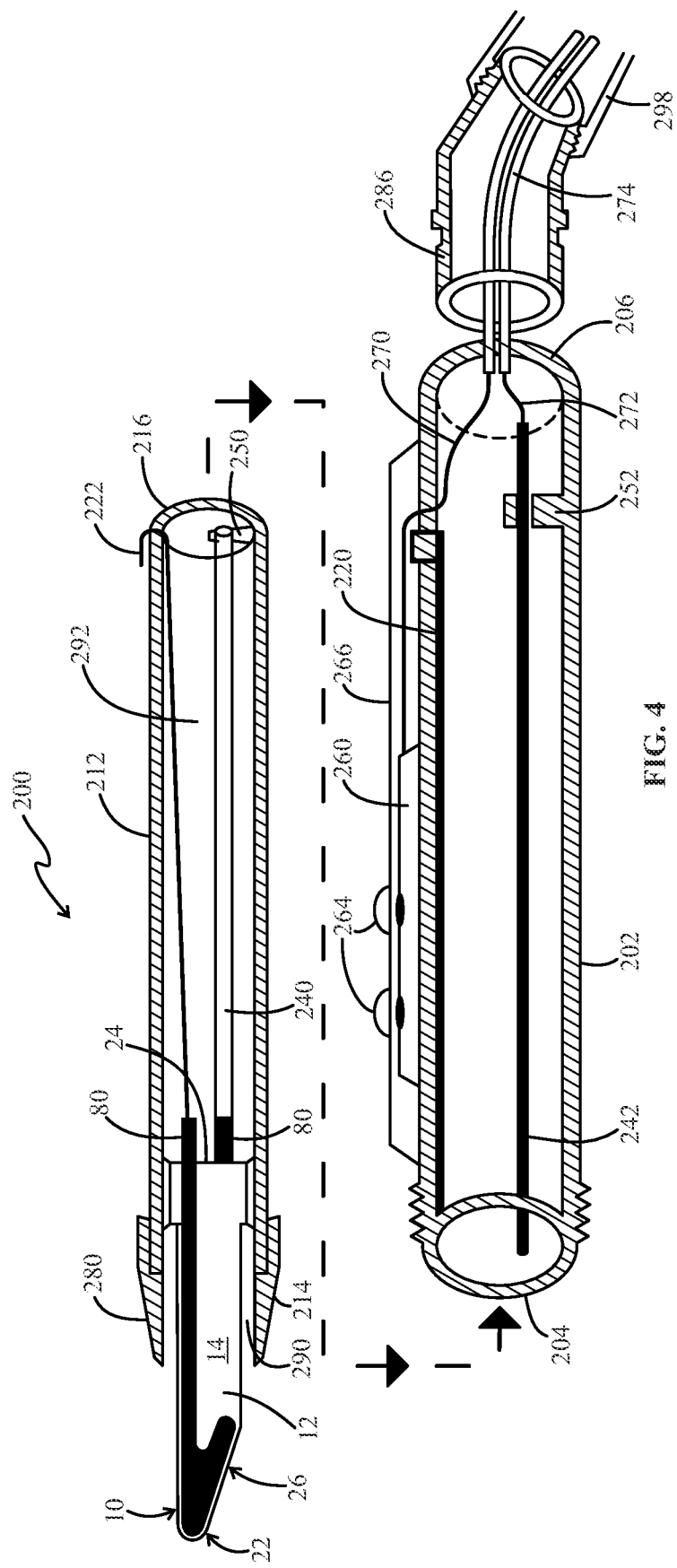
Figure 5:
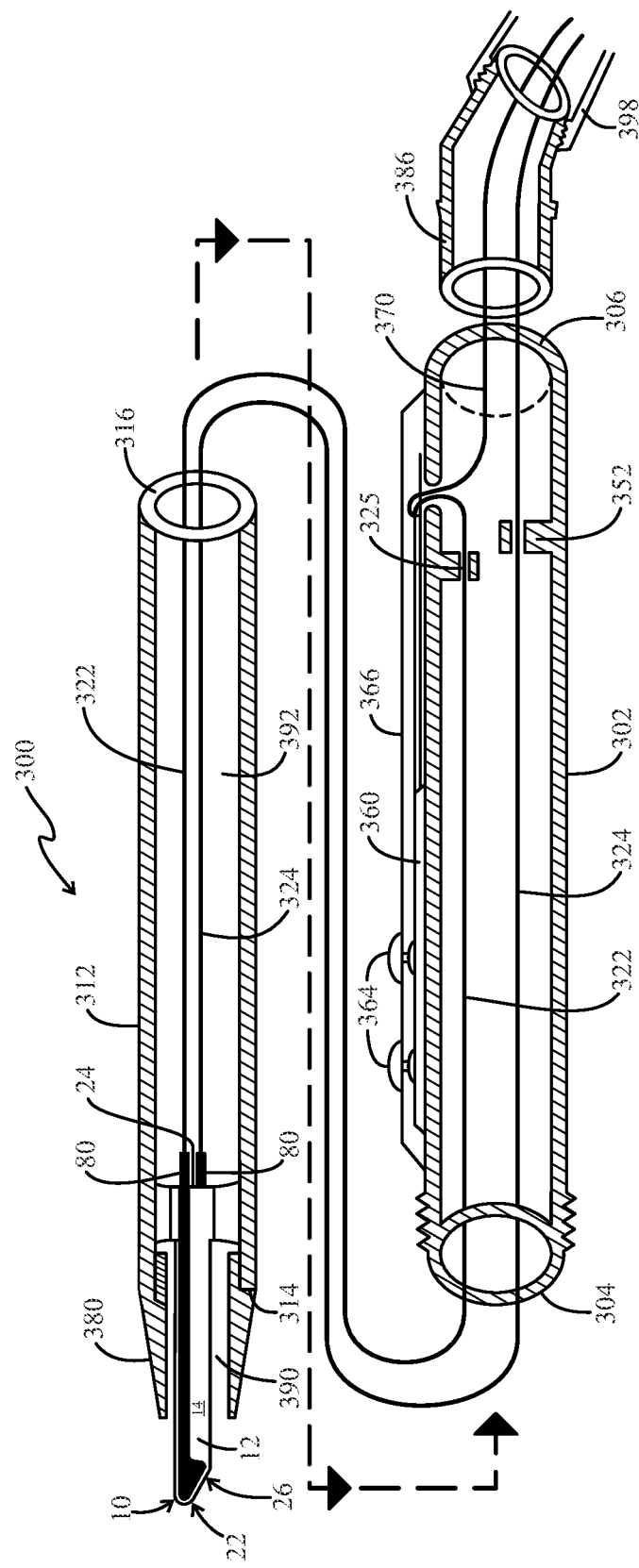

FIG. 4 is a side cross-sectional view showing separate components of another exemplary embodiment of the ultrapolar telescopic electrosurgery pencil of the present invention with the ultrapolar electrosurgery blade depicted in FIGS. 1 and 2 shown seated within the hollow telescopic member of the ultrapolar telescopic electrosurgery pencil of the present invention; and FIG. 5 is a side cross-sectional view showing separate components of yet another exemplary embodiment of the ultrapolar telescopic electrosurgery pencil of the present invention with the ultrapolar electrosurgery blade depicted in FIGS. 1 and 2 shown seated within the hollow telescopic member of the ultrapolar telescopic electrosurgery pencil of the present invention.

DETAILED DESCRIPTION OF EXEMPLARY EMBODIMENTS

The exemplary embodiments of the ultrapolar telescopic electrosurgery pencil for use in electrosurgical unit (ESU) monopolar and bipolar modes of the present invention enable a user or surgeon to perform cutting with the sharp non-conductive tip of the electrosurgery blade in the pencil as well as coagulation of large areas of biological tissue by using the electrical contacts of the electrosurgery blade. The ultrapolar telescopic electrosurgery pencil of the present invention may also perform cutting with the active and return electrodes of the electrosurgery blade. Exemplary embodiments of the ultrapolar telescopic electrosurgery pencil of the present invention include an ultrapolar electrosurgery blade that has a non-conductive member having first and second opposite planar sides and a sharp cutting edge, an active electrode positioned on the first opposite planar side of the non-conductive member such that at least a portion of the first opposite planar side is exposed near the cutting edge, and a return electrode positioned on the second opposite planar side of the non-conductive member such that at least a portion of the second opposite planar side is exposed near the cutting edge. The cutting edge of the non-conductive planar member can form a sharp non-conductive cutting edge for cutting biological tissue while the active and return electrodes located on opposite planar side of the non-conductive member can be used to perform coagulation as well as cutting of biological tissue.

The present invention is directed to an ultrapolar telescopic electrosurgery pencil which includes a handpiece member having a first end and a second end, a hollow telescopic member having a first end and a second end where the second end of the hollow telescopic member is concentrically positioned within the first end of the handpiece member, and an electrosurgery blade positioned within the first end of the hollow telescopic member where the electrosurgery blade includes a non-conductive member with opposing planar sides and a cutting edge, an active electrode positioned on one of the opposing planar sides such that at least a portion of the opposing planar side is exposed near the cutting edge, and a return electrode positioned on the other opposing planar side such that at least a portion of the other opposing planar side is exposed near the cutting edge.

The active electrode located on an opposing planar side of the non-conductive member may mirror at least a portion of the return electrode located on the other opposing planar side. Active and return electrodes on the electrosurgery blade can be conductive layers having a same thickness throughout. The top of the non-conductive member can be wider than the sharp cutting edge of the non-conductive member and the non-conductive member may be tapered from at least a portion of its top to a portion of its bottom.

The non-conductive planar member may comprise a ceramic and the active and return electrodes may comprise a stainless steel, a copper, and/or a tungsten. The active and return electrodes may each take the form of an elongated conductive layer that extends more than half the length of the non-conductive member. At least a portion of the elongated conductive layer of the active electrode may extend to, and along a partial length of, one or more opposing elongated edges of an opposing planar side of the non-conductive member and at least a portion of the elongated conductive layer of the return electrode may extend to, and along a partial length of, one or more opposing elongated edges of the other opposing planar side of the non-conductive member.

FIG. 1 is a side perspective view of an exemplary embodiment of an ultrapolar electrosurgery blade 10 used in the ultrapolar telescopic electrosurgery pencil of the present invention. Ultrapolar electrosurgery blade 10 includes non-conductive member 12 having first and second opposite planar sides 14, 16, a top 18, a bottom 20, a cutting end 22 with a sharp cutting edge 26, and a non-cutting end 24, and an active electrode 30 positioned on the first opposite planar side 14 of the non-conductive member 12 such that at least a portion of the first opposite planar side 14 is exposed near the sharp cutting edge 26. Angle X of sharp cutting edge 26 relative to a bottom portion of blade 10 may be less than 20 degrees as shown in FIG. 1. Ultrapolar electrosurgery blade 10 also includes conductive insert members 80 that are in communication with active and return electrodes contained on the non-conductive member. FIG. 1 shows the active electrode 30 on first opposite planar side 14 in communication with one of the conductive insert members 80 thereby making that conductive insert member a top active conductive insert member. Active electrode 30 may be a conductive layer that is deposited on the first opposite planar side 14 of the non-conductive member 12 and may comprise stainless steel, copper, and/or tungsten. As shown in FIG. 1, active electrode 30 is an elongated conductive layer that extends along a length of the first opposite planar side 14 of the non-conductive member 12 near the top 18 of the non-conductive member 12 with a "V" shaped hook like shape that is positioned on the first opposite planar side 14 of the non-conductive member 12 near the cutting end 22 of the non-conductive member 12. The active electrode 30 also extends along an entire length of the first opposite planar side 14 of the non-conductive member 12 to the non-cutting end 24 of the non-conductive member 12 and then wraps around the non-cutting end 24 of non-conductive member 12 so that active electrode 30 is in communication with one of conductive insert members 80. Non-conductive member 12 also includes openings (not shown) within the non-cutting end 24 for insertion of conductive insert members 80 and a rounded portion 94 which lies adjacent to an inner circumference of the ultrapolar telescopic electrosurgery pencil when the ultrapolar electrosurgery blade 10 is positioned within the ultrapolar telescopic electrosurgery pencil.

FIG. 2 is an opposite side view of the exemplary embodiment of the ultrapolar electrosurgery blade 10 shown in FIG. 1. Ultrapolar electrosurgery blade 10 includes non-conductive member 12 having first and second opposite planar sides 14, 16, a top 18, a bottom 20, a cutting end 22 with a sharp cutting edge 26, and a non-cutting end 24, and a return electrode 32 positioned on the second opposite planar side 16 of the non-conductive member 12 such that at least a portion of the second opposite planar side 16 is exposed near the sharp cutting edge 26. Ultrapolar electrosurgery blade 10 also includes conductive insert members 80 that are in communication with active and return electrodes contained on the non-conductive member 12. FIG. 2 shows the return electrode 32 on second opposite planar side 16 in communication with one of the conductive insert members 80 thereby making that conductive insert member a bottom return conductive insert member. Return electrode 32 may be a conductive layer that is deposited on the second opposite planar side 16 of the non-conductive member 12 and may comprise stainless steel, copper, and/or tungsten. As shown in FIG. 2, return electrode 32 is an elongated conductive layer that extends along a length of the second opposite planar side 16 of the non-conductive member 12 near the top 18 of the non-conductive member 12 with a "V" shaped hook like shape that is positioned on the second opposite planar side 16 of the non-conductive member 12 near the cutting end 22 of the non-conductive member 12. The return electrode 32 also extends along an entire length of the second opposite planar side 16 of the non-conductive member 12 to the non-cutting end 24 of the non-conductive member 12 and then wraps around the non-cutting end 24 of non-conductive member 12 so that return electrode 32 is in communication with one of conductive insert members 80. Non-conductive member 12 also includes openings (not shown) within the non-cutting end 24 for insertion of conductive insert members 80 and a rounded portion 94 which lies adjacent to an inner circumference of the ultrapolar telescopic electrosurgery pencil when the ultrapolar electrosurgery blade 10 is positioned within the ultrapolar telescopic electrosurgery pencil. Active electrode 30 and return electrode 32 located on first and second opposite planar sides 14, 16 of non-conductive member 12, respectively, are opposing mirror images of one another.

Figure 3:
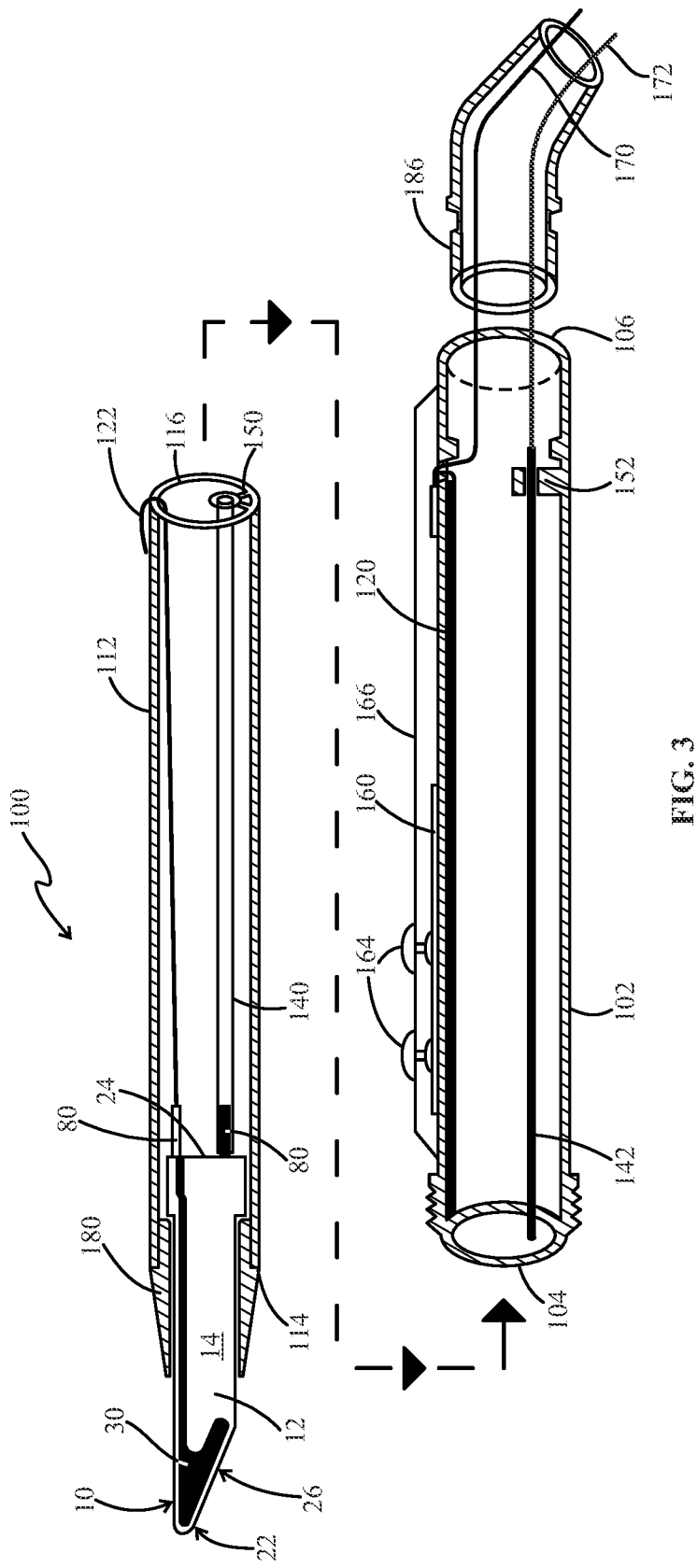
FIG. 3 is a side cross-sectional view showing separate components of one exemplary embodiment of the ultrapolar telescopic electrosurgery pencil of the present invention with the ultrapolar electrosurgery blade depicted in FIGS. 1 and 2 shown seated within the hollow telescopic member of the ultrapolar telescopic electrosurgery pencil of the present invention.

FIG. 3 is a side cross-sectional view showing separate components of one exemplary embodiment of the ultrapolar telescopic electrosurgery pencil 100 of the present invention with the ultrapolar electrosurgery blade 10 depicted in FIGS. 1 and 2 shown seated within the hollow telescopic member of the ultrapolar telescopic electrosurgery pencil 100 of the present invention. The ultrapolar telescopic electrosurgery pencil 100 includes a handpiece member 102 with first and second ends 104, 106, a hollow telescopic member 112 with first and second ends 114, 116 where the second end 116 of the hollow telescopic member 112 is concentrically positioned within (and retained within) the first end 104 of the handpiece member 102 when the ultrapolar telescopic electrosurgery pencil 100 is assembled for use. Ultrapolar telescopic electrosurgery pencil 100 also includes ultrapolar electrosurgery blade 10 positioned in the first end 104 of handpiece member 102. Ultrapolar electrosurgery blade 10 includes a non-conductive planar member 12 having opposing planar sides 14, 16, a cutting end 22 with a sharp cutting edge 26, an opposite non-cutting end 24, an active electrode 30 located on one opposing planar side 14 where at least a portion of the opposing planar side 14 is exposed near the non-conductive cutting end 22 of the non-conductive planar member 12, and a return electrode 32 (not shown as it is on the opposite side) located on the other opposing planar side 16 (not shown) where at least a portion of the other opposing planar side is exposed near the non-conductive cutting end 22 of the non-conductive planar member 12. Conductive insert members 80 are located at the non-cutting end 24 of the non-conductive planar member 12 and are in communication with the active and return electrodes 30, 32, respectively.

The ultrapolar telescopic electrosurgery pencil 100 also includes a conductive elongated contact member (which may take the form of a conductive channel) 120 attached to a top interior surface of handpiece member 102 and a conductive contact member 122 connected to the active electrode 30 of electrosurgery blade 10 through conductive insert member 80 such that a portion of the conductive contact member 122 is slidably engaged with conductive elongated contact member 120 contained within handpiece member 102 when the second end 116 of hollow telescopic member 112 is positioned within handpiece member 102. A portion of conductive contact member 122 may be positioned within an interior of hollow telescopic member 112 and a portion of conductive contact member 122 may be positioned on an exterior surface of hollow telescopic member 112. The ultrapolar telescopic electrosurgery pencil 100 also includes a hollow conductive tube member 140 contained within the hollow telescopic member 112 that is connected to return electrode (not shown) of electrosurgery blade 30 through conductive insert member 80 and a solid conductive rod member 142 contained within the handpiece member 102 so that solid conductive rod member 142 can slide within, and along a length of, hollow conductive tube member 140. A first support member 150 may be connected to hollow telescopic member 112 for retaining hollow conductive tube member 140 within hollow telescopic member 112 and a second support member 152 may be connected to handpiece member 102 for retaining solid conductive rod member 142 within handpiece member 102.

Conductive elongated contact member 120 is connected to a circuit board 160 via an electrical communication means such as a wire thereby connecting the active electrode 30 of ultrapolar electrosurgery blade 10 to circuit board 160. Communication means such as a wire 170 connects circuit board 160 to an electrosurgery unit (not shown) to provide power to the ultrapolar telescopic electrosurgery pencil 100 which can be operated via activation buttons 164 located on a top 166 of the electrosurgery pencil 100. Communication means such as a wire 172 may also be used to connect return electrode (not shown) to the electrosurgery unit (not shown) via the hollow conductive tube member 140 and the solid conductive rod member 142. The slidable engagement of the conductive contact member 122 with the conductive elongated contact member 120 and the slidable engagement of the solid conductive rod member 142 within the hollow conductive tube member 140 enables telescoping of the hollow telescopic member 112 with respect to the handpiece member 102. This allows a surgeon or user to lengthen or shorten the ultrapolar telescopic electrosurgery pencil to better facilitate its use depending on the type and area of the electrosurgery being performed.

The ultrapolar telescopic electrosurgery pencil 100 also includes a nozzle member 180 connected to the first end 114 of the hollow telescopic member 112 so that at least a portion of the ultrapolar electrosurgery blade 10 is contained within the nozzle member 180 and the first end 114 of the hollow telescopic member 112. Nozzle member 180 may be transparent and functions to funnel smoke and/or debris into a smoke evacuation channel of the ultrapolar telescopic electrosurgery pencils that include smoke evacuation channels such as those embodiments shown in FIGS. 4 and 5. Ultrapolar telescopic electrosurgery pencil 100 also includes a swivel member 186 connected to the second end 106 of the handpiece member 102.

FIG. 4 is a side cross-sectional view showing separate components of another exemplary embodiment of the ultrapolar telescopic electrosurgery pencil 200 of the present invention with the ultrapolar electrosurgery blade 10 depicted in FIGS. 1 and 2 shown seated within the hollow telescopic member of the ultrapolar telescopic electrosurgery pencil of the present invention. The main differences between the embodiment shown in FIG. 3 and this embodiment is that this embodiment of the ultrapolar telescopic electrosurgery pencil 200 includes a smoke evacuation channel and the active and return contacts of the ultrapolar electrosurgery blade are eventually connected to active and return wires that are both contained within an insulated power cord which is used to connect the ultrapolar telescopic electrosurgery pencil 200 to an electrosurgery unit/ electrosurgery unit generator (ESU).

The ultrapolar telescopic electrosurgery pencil 200 includes a handpiece member 202 with first and second ends 204, 206, a hollow telescopic member 212 with first and second ends 214, 216 where the second end 216 of the hollow telescopic member 212 is concentrically positioned within (and retained within) the first end 204 of the handpiece member 202 when the ultrapolar telescopic electrosurgery pencil 200 is assembled for use. Ultrapolar telescopic electrosurgery pencil 200 also includes ultrapolar electrosurgery blade 10 positioned in the first end 204 of handpiece member 202. Ultrapolar electrosurgery blade 10 includes a non-conductive planar member 12 having opposing planar sides 14, 16, a cutting end 22 with a sharp cutting edge 26, an opposite non-cutting end 24, an active electrode 30 located on one opposing planar side 14 where at least a portion of the opposing planar side 14 is exposed near the non-conductive cutting end 22 of the non-conductive planar member 12, and a return electrode 32 (not shown as it is on the opposite side) located on the other opposing planar side 16 (not shown) where at least a portion of the other opposing planar side is exposed near the non-conductive cutting end 22 of the non-conductive planar member 12. Conductive insert members 80 are located at the non-cutting end 24 of the non-conductive planar member 12 and are in communication with the active and return electrodes 30, 32, respectively.

The ultrapolar telescopic electrosurgery pencil 200 also includes a conductive elongated contact member (which may take the form of a conductive channel) 220 attached to a top interior surface of handpiece member 202 and a conductive contact member 222 connected to the active electrode 30 of electrosurgery blade 10 through conductive insert member 80 such that a portion of the conductive contact member 222 is slidably engaged with conductive elongated contact member 220 contained within handpiece member 202 when the second end 216 of hollow telescopic member 212 is positioned within handpiece member 202. A portion of conductive contact member 222 may be positioned within an interior of hollow telescopic member 212 and a portion of conductive contact member 222 may be positioned on an exterior surface of hollow telescopic member 212. The ultrapolar telescopic electrosurgery pencil 200 also includes a hollow conductive tube member 240 contained within the hollow telescopic member 212 that is connected to return electrode (not shown) of electrosurgery blade 30 through conductive insert member 80 and a solid conductive rod member 242 contained within the handpiece member 202 so that solid conductive rod member 242 can slide within, and along a length of, hollow conductive tube member 240. A first support member 250 may be connected to hollow telescopic member 212 for retaining hollow conductive tube member 240 within hollow telescopic member 212 and a second support member 252 may be connected to handpiece member 202 for retaining solid conductive rod member 242 within handpiece member 202.

Conductive elongated contact member 220 is connected to a circuit board 260 via an electrical communication means such as a wire thereby connecting the active electrode 30 of ultrapolar electrosurgery blade 10 to circuit board 260. Communication means such as a wire 270 connects circuit board 260 to an electrosurgery unit (not shown) to provide power to the ultrapolar telescopic electrosurgery pencil 200 which can be operated via activation buttons 264 located on a top 266 of the electrosurgery pencil 200. Communication means such as a wire 272 may also be used to connect return electrode (not shown) to the electrosurgery unit (not shown) via the hollow conductive tube member 240 and the solid conductive rod member 242. Wires 270 and 272 are contained within an insulated power cord 274 which provides for easier connection of the ultrapolar telescopic electrosurgery pencil 200 to the different monopolar and bipolar connection modes on the electrosurgical unit (ESU). The slidable engagement of the conductive contact member 222 with the conductive elongated contact member 220 and the slidable engagement of the solid conductive rod member 242 within the hollow conductive tube member 240 enables telescoping of the hollow telescopic member 212 with respect to the handpiece member 202. This allows a surgeon or user to lengthen or shorten the ultrapolar telescopic electrosurgery pencil to better facilitate its use depending on the type and area of the electrosurgery being performed.

The ultrapolar telescopic electrosurgery pencil 200 also includes a nozzle member 280 connected to the first end 214 of the hollow telescopic member 212 so that at least a portion of the ultrapolar electrosurgery blade 10 is contained within the nozzle member 280 and the first end 214 of the hollow telescopic member 212. Nozzle member 280 may be transparent and functions to funnel smoke and/or debris into a smoke evacuation channel 292 from the area 290 within nozzle 280 surrounding blade 10. Ultrapolar telescopic electrosurgery pencil 200 also includes a swivel member 286 having one end connected to the second end 206 of the handpiece member 202 and the other end connectable to a vacuum tube 298 for evacuating smoke and debris from the surgical site. In this embodiment of the ultrapolar telescopic electrosurgery pencil 200, the nozzle 280, the hollow telescopic member 212, the handpiece member 202, and the swivel member 286 together form a smoke evacuation channel contained within the ultrapolar telescopic electrosurgery pencil 200.

FIG. 5 is a side cross-sectional view showing separate components of yet another exemplary embodiment of the ultrapolar telescopic electrosurgery pencil 300 of the present invention with the ultrapolar electrosurgery blade depicted in FIGS. 1 and 2 shown seated within the hollow telescopic member of the ultrapolar telescopic electrosurgery pencil 300 of the present invention. The main difference between the embodiment shown in FIG. 4 and this embodiment is that this embodiment of the ultrapolar telescopic electrosurgery pencil 300 does not use any slidable engagement means within the hollow telescopic member and the handpiece member to connect to the active and return electrodes of the electrosurgery blade 10.

The ultrapolar telescopic electrosurgery pencil 300 includes a handpiece member 302 with first and second ends 304, 306, a hollow telescopic member 312 with first and second ends 314, 316 where the second end 316 of the hollow telescopic member 312 is concentrically positioned within (and retained within) the first end 304 of the handpiece member 302 when the ultrapolar telescopic electrosurgery pencil 300 is assembled for use. Ultrapolar telescopic electrosurgery pencil 300 also includes ultrapolar electrosurgery blade 10 positioned in the first end 304 of handpiece member 302. Ultrapolar electrosurgery blade 10 includes a non-conductive planar member 12 having opposing planar sides 14, 16, a cutting end 22 with a sharp cutting edge 26, an opposite non-cutting end 24, an active electrode 30 located on one opposing planar side 14 where at least a portion of the opposing planar side 14 is exposed near the non-conductive cutting end 22 of the non-conductive planar member 12, and a return electrode 32 (not shown as it is on the opposite side) located on the other opposing planar side 16 (not shown) where at least a portion of the other opposing planar side is exposed near the non-conductive cutting end 22 of the non-conductive planar member 12. Conductive insert members 80 are located at the non-cutting end 24 of the non-conductive planar member 12 and are in communication with the active and return electrodes 30, 32, respectively.

The ultrapolar telescopic electrosurgery pencil 300 also includes a first insulated wire 322 connected to the active electrode of electrosurgery blade 10 and a first retaining element 325 for retaining at least a portion of the first insulated wire 322 near a top interior of the handpiece member 302 and a second insulated wire 324 connected to the return electrode of the electrosurgery blade 10 and a second retaining element 352 for retaining at least a portion of the second insulated wire 324 near a bottom interior of the handpiece member 302.

First insulated wire 322 is connected to a circuit board 360 thereby connecting the active electrode 30 of ultrapolar electrosurgery blade 10 to circuit board 360. Communication means such as a wire 370 connects circuit board 360 to an electrosurgery unit (not shown) to provide power to the ultrapolar telescopic electrosurgery pencil 300 which can be operated via activation buttons 364 located on a top 366 of the electrosurgery pencil 300. Second insulated wire 324 connects return electrode (not shown) to the electrosurgery unit (not shown). First and second insulated wires 322, 324 move freely within the hollow telescopic member 312 and the handpiece member 302 when a surgeon or user lengthens or shortens the ultrapolar telescopic electrosurgery pencil by extending or retracting the hollow telescopic member 322 from or into the handpiece member 302.

The ultrapolar telescopic electrosurgery pencil 300 also includes a nozzle member 380 connected to the first end 314 of the hollow telescopic member 312 so that at least a portion of the ultrapolar electrosurgery blade 10 is contained within the nozzle member 380 and the first end 314 of the hollow telescopic member 312. Nozzle member 380 may be transparent and functions to funnel smoke and/or debris into a smoke evacuation channel 392 from the area 390 within nozzle 380 surrounding blade 10. Ultrapolar telescopic electrosurgery pencil 300 also includes a swivel member 386 having one end connected to the second end 306 of the handpiece member 302 and the other end connectable to a vacuum tube 398 for evacuating smoke and debris from the surgical site. In this embodiment of the ultrapolar telescopic electrosurgery pencil 300, the nozzle 380, the hollow telescopic member 312, the handpiece member 302, and the swivel member 386 together form a smoke evacuation channel contained within the ultrapolar telescopic electrosurgery pencil 300.

It should be understood that variations of the separate components that comprise the different embodiments of the ultrapolar telescopic electrosurgery pencil can be mixed and matched to create any number of embodiments of the ultrapolar telescopic electrosurgery pencil of the present invention. For example, the power cord shown in FIG. 4 that contains insulated active and return electrode wires may be used in the embodiment of the ultrapolar telescopic electrosurgery pencil shown in FIG. 3 as well as in the embodiment of the ultrapolar telescopic electrosurgery pencil shown in FIG. 5 to create two more exemplary embodiments of the ultrapolar telescopic electrosurgery pencil of the present invention. In yet another unlimiting example, the ultrapolar electrosurgery blade shown in FIG. 3 may be seated within the hollow telescopic member of the ultrapolar telescopic electrosurgery pencil using a seating member like the one shown in FIG. 4 so that smoke and debris can be evacuated away from the surgical site, around the ultrapolar electrosurgery blade, and through the open channels in the hollow telescopic member and the handpiece member thereby creating still another exemplary embodiment of the ultrapolar telescopic electrosurgery pencil of the present invention.

The handpiece member of the ultrapolar telescopic electrosurgery pencil may include only one activation button for coagulation since the sharp cutting end/edge of the nonconductive planar member can make precise cuts without having power applied to the ultrapolar electrosurgery blade. Alternatively, the handpiece may include more than one activation button for cutting and coagulation.

The ultrapolar telescopic electrosurgery pencil of the present invention may be used in a monopolar mode or a bipolar mode when used to perform electrosurgery. The ultrapolar telescopic electrosurgery pencil may be capable of cutting and coagulating tissue at power levels of less than 20 Watts and may perform particularly well at 15 Watts.

Features and Advantages of the Ultrapolar Telescopic Electrosurgery Pencil

The conductive layers that make up the active and return electrodes located on opposing sides of the non-conductive planar member may take on any number of configurations while still enabling the electrosurgery blade to function at very low power levels (such as 15-20 Watts or even less) while cutting and coagulating tissue. The ultrapolar telescopic electrosurgery pencil of the present invention can operate and function using low power because the tissue resistance is greatly reduced by not having current go through the patient's body. Unlike other electrosurgery pencils, the ultrapolar telescopic electrosurgery pencil of the present invention does not require the placement of a return electrode pad on the patient's body. As a result, no radio frequency current is passing through the patient's body so the body resistance is almost zero. Therefore, the present invention is much safer than other electrosurgery pencils because the patient is not at risk of being burned by the return electrode since no return electrode is placed on the patient and no current is passing through the body of the patient.

The sharp cutting edge of the ultrapolar electrosurgery blade of the ultrapolar telescopic electrosurgery pencil can cut tissue without applying power to the ultrapolar telescopic electrosurgery pencil and can also cut and coagulate tissue when power is applied to the ultrapolar telescopic electrosurgery pencil.

The ultrapolar telescopic electrosurgery pencil of the present invention stops tissue from bleeding after cutting with minimal or no lateral damage to the tissue and without charring or burning of the tissue. Further, tissue does not stick to the ultrapolar electrosurgery blade of the ultrapolar telescopic electrosurgery pencil while cutting and/or coagulating tissue. In addition, very little smoke is produced when using the ultrapolar telescopic electrosurgery pencil due to the low or reduced power required for the ultrapolar telescopic electrosurgery pencil to function and the minimal or non-existent charring of tissue.

The ultrapolar telescopic electrosurgery pencil of the present invention can be used in both monopolar and bipolar modes thereby providing an electrosurgery pencil that can be used with almost any electrosurgical unit. In addition, the telescopic feature (i.e. the hollow telescopic member) enables a user surgeon to extend or reduce the length of ultrapolar electrosurgery pencil depending on the particular surgical procedure being performed.

The above exemplary embodiments are not intended to limit the scope, applicability, or configuration of the invention in any way. Rather, the disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

The invention claimed is:

1. An ultrapolar telescopic electrosurgery pencil comprising:
   a handpiece member having a first end and a second end;
   a hollow telescopic member having a first end and a second end wherein the second end of the hollow telescopic member is concentrically positioned within the first end of the handpiece member; and
   an electrosurgery blade positioned at least partially within the first end of the hollow telescopic member wherein the electrosurgery blade includes a non-conductive member with a top, a bottom, opposing planar sides located between the top and the bottom, and a sharp angled cutting edge angled upward relative to the bottom of the non-conductive member, an active electrode positioned on one of the opposing planar sides such that at least a portion of the opposing planar side is exposed directly above an entire length of the sharp angled cutting edge and below the active electrode, and a return electrode positioned on the other opposing planar side such that at least a portion of the other opposing planar side is exposed directly above the sharp angled cutting edge and below the return electrode.

2. The ultrapolar telescopic electrosurgery pencil of claim 1 wherein the electrosurgery pencil can be used in both a monopolar mode and a bipolar mode when used to perform electrosurgery.

3. The ultrapolar telescopic electrosurgery pencil of claim 1 wherein the electrosurgery pencil is capable of cutting and coagulating tissue at a power level of less than twenty watts.

4. The ultrapolar telescopic electrosurgery pencil of claim 1 further comprising a retaining member located within the hollow telescopic member for retaining at least a portion of the electrosurgery blade within the hollow telescopic member.

5. The ultrapolar telescopic electrosurgery pencil of claim 1 further comprising a first insulated wire connected to the active electrode of the electrosurgery blade and a first retaining element for retaining at least a portion of the first insulated wire near a top interior of the handpiece member.

6. The ultrapolar telescopic electrosurgery pencil of claim 5 further comprising a second insulated wire connected to the return electrode of the electrosurgery blade and a second retaining element for retaining at least a portion of the second insulated wire near a bottom interior of the handpiece member.

7. The ultrapolar telescopic electrosurgery pencil of claim 6 wherein the handpiece member and the hollow telescopic member form an evacuation channel for evacuating at least one of smoke and debris away from a surgical site where the electrosurgery pencil is being employed.

8. The ultrapolar telescopic electrosurgery pencil of claim 7 further comprising a swivel member connected to the second end of the handpiece member.

9. The ultrapolar telescopic electrosurgery pencil of claim 7 further comprising a nozzle member connected to the first end of the hollow telescopic member wherein at least a portion of the electrosurgery blade is positioned within the nozzle member.

10. The ultrapolar telescopic electrosurgery pencil of claim 9 wherein the nozzle member, the handpiece member, and the hollow telescopic member form the evacuation channel for evacuating at least one of smoke and debris away from the surgical site where the electrosurgery pencil is being employed.

11. The ultrapolar telescopic electrosurgery pencil of claim 1 further comprising a conductive elongated contact member attached to a top interior surface of the handpiece member and a conductive contact member connected to the active electrode of the electrosurgery blade such that the conductive contact member can be slidably engaged with respect to the conductive elongated contact member.

12. The ultrapolar telescopic electrosurgery pencil of claim 11 further comprising a hollow conductive tube member contained within the hollow telescopic member that is connected to the return electrode of the electrosurgery blade and a solid conductive rod member contained within the handpiece member such that the solid conductive rod member can slide within and along a length of the hollow conductive tube member.

13. The ultrapolar telescopic electrosurgery pencil of claim 12 wherein the handpiece member and the hollow telescopic member form an evacuation channel for evacuating at least one of smoke and debris away from a surgical site where the electrosurgery pencil is being employed.

14. The ultrapolar telescopic electrosurgery pencil of claim 12 further comprising a swivel member connected to the second end of the handpiece member.

15. The ultrapolar telescopic electrosurgery pencil of claim 12 further comprising a nozzle member connected to the first end of the hollow telescopic member wherein at least a portion of the electrosurgery blade is positioned within the nozzle member.

16. The ultrapolar telescopic electrosurgery pencil of claim 15 wherein the nozzle member, the handpiece member, and the hollow telescopic member form an evacuation channel for evacuating at least one of smoke and debris away from a surgical site where the electrosurgery pencil is being employed.

17. The ultrapolar telescopic electrosurgery pencil of claim 16 further comprising a hollow swivel member having a first end connected to the second end of the handpiece member and a second end capable of being connected to a vacuum tube.

18. The ultrapolar telescopic electrosurgery pencil of claim 11 wherein at least a portion of the conductive contact member is positioned within an interior of the hollow telescopic member and at least a portion of the conductive contact member is positioned on an exterior surface of the hollow telescopic member.

19. An ultrapolar telescopic electrosurgery pencil comprising:

a handpiece member having a first end and a second end;
a hollow telescopic member having a first end and a second end wherein the second end of the hollow telescopic member is concentrically positioned within the first end of the handpiece member;
an electrosurgery blade positioned at least partially within the first end of the hollow telescopic member wherein the electrosurgery blade includes a non-conductive member with a top, a bottom, opposing planar sides located between the top and the bottom, and a sharp angled cutting edge angled upward relative to the bottom of the non-conductive member, an active electrode positioned on one of the opposing planar sides such that at least a portion of the opposing planar side is exposed directly above an entire length of the sharp angled cutting edge and below the active electrode, and a return electrode positioned on the other opposing planar side such that at least a portion of the other opposing planar side is exposed directly above the sharp angled cutting edge and below the return electrode;
a first insulated wire connected to the active electrode of the electrosurgery blade and a first retaining element for retaining at least a portion of the first insulated wire near a top interior of the handpiece member; and
a second insulated wire connected to the return electrode of the electrosurgery blade and a second retaining element for retaining at least a portion of the second insulated wire near a bottom interior of the handpiece member.

20. An ultrapolar telescopic electrosurgery pencil comprising:

a handpiece member having a first end and a second end;
a hollow telescopic member having a first end and a second end wherein the second end of the hollow telescopic member is concentrically positioned within the first end of the handpiece member;
an electrosurgery blade positioned at least partially within the first end of the hollow telescopic member wherein the electrosurgery blade includes a non-conductive member with a top, a bottom, opposing planar sides located between the top and the bottom, and a sharp angled cutting edge angled upward relative to the bottom of the non-conductive member, an active electrode positioned on one of the opposing planar sides such that at least a portion of the opposing planar side is exposed directly above an entire length of the sharp angled cutting edge and below the active electrode, and a return electrode positioned on the other opposing planar side such that at least a portion of the other opposing planar side is exposed directly above the sharp angled cutting edge and below the return electrode;
a conductive elongated contact member attached to a top interior surface of the handpiece member and a conductive contact member connected to the active electrode of the electrosurgery blade such that the conductive contact member can be slidably engaged with respect to the conductive elongated contact member; and
a hollow conductive tube member contained within the hollow telescopic member that is connected to the return electrode of the electrosurgery blade and a solid conductive rod member contained within the handpiece member such that the solid conductive rod member can slide within and along a length of the hollow conductive tube member.

* * * * *